United States Patent
Halperin et al.

(10) Patent No.: US 8,099,151 B2
(45) Date of Patent: *Jan. 17, 2012

(54) SYSTEM AND METHOD FOR MAGNETIC-RESONANCE-GUIDED ELECTROPHYSIOLOGIC AND ABLATION PROCEDURES

(75) Inventors: Henry R Halperin, Baltimore, MD (US); Ronald D. Berger, Baltimore, MD (US); Ergin Atalar, Columbia, MD (US); Elliot R McVeigh, Potomac, MD (US); Albert Lardo, Baldwin, MD (US); Hugh Calkins, Baltimore, MD (US); Joao Lima, Timonium, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 1548 days.

This patent is subject to a terminal disclaimer.

(21) Appl. No.: 11/314,241

(22) Filed: Dec. 22, 2005

(65) Prior Publication Data

US 2006/0100506 A1    May 11, 2006

Related U.S. Application Data

(60) Continuation of application No. 10/424,093, filed on Apr. 28, 2003, now Pat. No. 7,155,271, which is a division of application No. 09/428,990, filed on Oct. 29, 1999, now Pat. No. 6,701,176.

(60) Provisional application No. 60/106,965, filed on Nov. 4, 1998.

(51) Int. Cl.
*A61B 5/05*    (2006.01)

(52) U.S. Cl. .................. 600/423; 600/410; 600/424

(58) Field of Classification Search .......... 600/410–423, 600/407; 607/119–123; 324/307, 309, 318
See application file for complete search history.

(56) References Cited

U.S. PATENT DOCUMENTS 3,871,382 A    3/1975 Mann
3,968,802 A    7/1976 Ballis
(Continued)

FOREIGN PATENT DOCUMENTS

EP    0 243 573 A2    11/1987
(Continued)

OTHER PUBLICATIONS

Ackerman "Rapd 3D Tracking of Small RF Coils", Proceedings fo the 5th Annual Meeting of SMRM, Montreal Canada (1986), pp. 1131-1132.
(Continued)

*Primary Examiner* — Tse Chen
*Assistant Examiner* — Baisakhi Roy
(74) *Attorney, Agent, or Firm* — Nixon & Vanderhye P.C.

(57)    ABSTRACT

A system and method for using magnetic resonance imaging to increase the accuracy of electrophysiologic procedures includes an invasive combined electrophysiology and imaging antenna catheter which includes an RF antenna for receiving magnetic resonance signals and diagnostic electrodes for receiving electrical potentials. The combined electrophysiology and imaging antenna catheter is used in combination with a magnetic resonance imaging scanner to guide and provide visualization during electrophysiologic diagnostic or therapeutic procedures, such as ablation of cardiac arrhythmias. The combined electrophysiology and imaging antenna catheter may further include an ablation tip, and be used as an intracardiac device to deliver energy to selected areas of tissue and visualize the resulting ablation lesions. The antenna utilized in the combined electrophysiology and imaging catheter for receiving MR signals is preferably of the coaxial or "loopless" type. High-resolution images from the antenna may be combined with low-resolution images from surface coils of the MR scanner to produce a composite image. A system for eliminating the pickup of RF energy in which intracardiac wires are detuned by filtering so that they become very inefficient antennas. An RF filtering system is provided for suppressing the MR imaging signal while not attenuating the RF ablative current. Steering means may be provided for steering the invasive catheter under MR guidance. Other ablative methods can be used such as laser, ultrasound, and low temperatures.

35 Claims, 3 Drawing Sheets

U.S. PATENT DOCUMENTS

| | | |
|---|---|---|
| 4,295,467 A | 10/1981 | Mann et al. |
| 4,431,005 A | 2/1984 | McCormick |
| 4,445,501 A | 5/1984 | Bresler |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,682,125 A | 7/1987 | Harrison et al. |
| 4,689,621 A | 8/1987 | Kleinberg |
| 4,754,752 A | 7/1988 | Ginsburg et al. |
| 4,757,820 A | 7/1988 | Itoh |
| 4,766,381 A | 8/1988 | Conturo et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,623 A | 8/1989 | Bradshaw et al. |
| 4,859,950 A | 8/1989 | Keren |
| 4,932,411 A | 6/1990 | Fritschy et al. |
| 4,951,672 A | 8/1990 | Buchwald et al. |
| 4,960,106 A | 10/1990 | Kubokawa et al. |
| 4,989,608 A | 2/1991 | Ratner |
| 5,019,075 A | 5/1991 | Spears et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,170,789 A | 12/1992 | Narayan et al. |
| 5,178,618 A | 1/1993 | Kandarpa |
| 5,190,046 A | 3/1993 | Shturman |
| 5,209,233 A | 5/1993 | Holland et al. |
| 5,211,165 A | 5/1993 | Dumoulin et al. |
| 5,217,010 A | 6/1993 | Tsitlik et al. |
| 5,246,438 A | 9/1993 | Langberg |
| 5,251,635 A | 10/1993 | Dumoulin et al. |
| 5,271,400 A | 12/1993 | Dumoulin |
| 5,300,108 A | 4/1994 | Rebell et al. |
| 5,307,808 A | 5/1994 | Dumoulin et al. |
| 5,307,814 A | 5/1994 | Kressel et al. |
| 5,315,025 A | 5/1994 | Bushell et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,333,095 A | 7/1994 | Stevenson et al. |
| 5,334,193 A | 8/1994 | Nardella |
| 5,348,010 A | 9/1994 | Schnall et al. |
| 5,352,979 A | 10/1994 | Conturo |
| 5,353,795 A | 10/1994 | Souza et al. |
| 5,355,087 A | 10/1994 | Claiborne et al. |
| 5,358,515 A | 10/1994 | Hürter et al. |
| 5,363,845 A | 11/1994 | Chowdhury et al. |
| 5,370,644 A | 12/1994 | Langberg |
| 5,377,678 A | 1/1995 | Dumoulin et al. |
| 5,391,199 A | 2/1995 | Ben-Haim |
| 5,398,683 A | 3/1995 | Edwards et al. |
| 5,400,787 A | 3/1995 | Marandos |
| 5,413,104 A | 5/1995 | Buijs et al. |
| 5,419,325 A | 5/1995 | Dumoulin et al. |
| 5,433,198 A | 7/1995 | Desai |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rinehart et al. |
| 5,462,055 A | 10/1995 | Casey et al. |
| 5,476,095 A | 12/1995 | Schnall et al. |
| 5,480,422 A | 1/1996 | Ben-Haim |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,540,959 A | 7/1996 | Wang |
| 5,545,201 A | 8/1996 | Helland et al. |
| 5,558,093 A | 9/1996 | Pomeranz |
| 5,577,502 A | 11/1996 | Darrow et al. |
| 5,578,008 A | 11/1996 | Hara |
| 5,588,432 A | 12/1996 | Crowley |
| 5,590,657 A | 1/1997 | Cain et al. |
| 5,620,476 A | 4/1997 | Truex et al. |
| 5,623,241 A | 4/1997 | Minkoff |
| 5,629,622 A | 5/1997 | Scampini |
| 5,644,234 A | 7/1997 | Rasche et al. |
| 5,647,361 A | 7/1997 | Damadian |
| 5,662,108 A | 9/1997 | Budd et al. |
| 5,671,739 A | 9/1997 | Darrow et al. |
| 5,682,897 A | 11/1997 | Pomeranz |
| 5,685,878 A | 11/1997 | Falwell et al. |
| 5,697,958 A | 12/1997 | Paul et al. |
| 5,699,801 A | 12/1997 | Atalar et al. |
| 5,706,810 A | 1/1998 | Rubinsky et al. |
| 5,715,822 A | 2/1998 | Watkins et al. |
| 5,715,825 A | 2/1998 | Crowley |
| 5,716,390 A | 2/1998 | Li |
| 5,722,998 A | 3/1998 | Prutchi et al. |
| 5,738,096 A | 4/1998 | Ben-Haim |
| 5,741,321 A | 4/1998 | Brennen |
| 5,749,835 A | 5/1998 | Glantz |
| 5,751,539 A | 5/1998 | Stevenson et al. |
| 5,759,202 A | 6/1998 | Schroeppel |
| 5,769,800 A | 6/1998 | Gelfand et al. |
| 5,775,338 A | 7/1998 | Hastings |
| 5,779,669 A | 7/1998 | Haissaguerre et al. |
| 5,782,891 A | 7/1998 | Hassler et al. |
| 5,792,055 A | 8/1998 | McKinnon |
| 5,827,997 A | 10/1998 | Chung et al. |
| 5,833,608 A | 11/1998 | Acker |
| 5,836,992 A | 11/1998 | Thompson et al. |
| 5,840,025 A | 11/1998 | Ben-Haim |
| 5,840,031 A | 11/1998 | Crowley |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,896,267 A | 4/1999 | Hittman et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,004,269 A | 12/1999 | Crowley et al. |
| 6,008,980 A | 12/1999 | Stevenson et al. |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,055,457 A | 4/2000 | Bonner |
| 6,066,136 A | 5/2000 | Geistert |
| 6,101,417 A | 8/2000 | Vogel et al. |
| 6,128,522 A | 10/2000 | Acker et al. |
| 6,129,670 A | 10/2000 | Burdette et al. |
| 6,141,594 A | 10/2000 | Flynn et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,226,545 B1 | 5/2001 | Gilderdale |
| 6,236,205 B1 | 5/2001 | Luedeke et al. |
| 6,238,390 B1 | 5/2001 | Tu et al. |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,971 B1 | 9/2001 | Atalar et al. |
| 6,332,089 B1 | 12/2001 | Acker et al. |
| 6,390,996 B1 | 5/2002 | Halperin et al. |
| 6,408,202 B1 | 6/2002 | Lima et al. |
| 6,414,835 B1 | 7/2002 | Wolf et al. |
| 6,424,234 B1 | 7/2002 | Stevenson |
| 6,428,537 B1 | 8/2002 | Swanson et al. |
| 6,456,481 B1 | 9/2002 | Stevenson |

| | | |
|---|---|---|
| 6,459,935 B1 | 10/2002 | Piersma |
| 6,473,291 B1 | 10/2002 | Stevenson |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,549,800 B1 | 4/2003 | Atalar et al. |
| 6,556,009 B2 | 4/2003 | Kellman et al. |
| 6,566,978 B2 | 5/2003 | Stevenson et al. |
| 6,567,259 B2 | 5/2003 | Stevenson et al. |
| 6,567,703 B1 | 5/2003 | Thompson et al. |
| 6,593,884 B1 | 7/2003 | Gilboa et al. |
| 6,606,513 B2 | 8/2003 | Lardo et al. |
| 6,628,980 B2 | 9/2003 | Atalar et al. |
| 6,633,780 B1 | 10/2003 | Berger |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,779 B2 | 1/2004 | King et al. |
| 6,687,550 B1 | 2/2004 | Doan |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,765,780 B2 | 7/2004 | Brendel et al. |
| 6,771,067 B2 | 8/2004 | Kellman et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,876,885 B2 | 4/2005 | Swoyer et al. |
| 6,882,248 B2 | 4/2005 | Stevenson et al. |
| 6,898,454 B2 | 5/2005 | Atalar et al. |
| 6,904,307 B2 | 6/2005 | Karmarkar et al. |
| 6,925,328 B2 | 8/2005 | Foster et al. |
| 6,931,286 B2 | 8/2005 | Sigg et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,999,818 B2 | 2/2006 | Stevenson et al. |
| 7,012,192 B2 | 3/2006 | Stevenson et al. |
| 7,013,180 B2 | 3/2006 | Villaseca et al. |
| 7,038,900 B2 | 5/2006 | Stevenson et al. |
| 7,047,074 B2 | 5/2006 | Connelly et al. |
| 7,092,766 B1 | 8/2006 | Salys et al. |
| 7,113,387 B2 | 9/2006 | Stevenson et al. |
| 7,133,714 B2 | 11/2006 | Karmarkar et al. |
| 7,155,271 B2 | 12/2006 | Halperin et al. |
| 7,236,816 B2 | 6/2007 | Kumar et al. |
| 7,310,216 B2 | 12/2007 | Stevenson et al. |
| 7,363,090 B2 | 4/2008 | Halperin et al. |
| 7,412,276 B2 | 8/2008 | Halperin et al. |
| 7,422,568 B2 | 9/2008 | Yang et al. |
| 2002/0040185 A1 | 4/2002 | Atalar et al. |
| 2002/0055678 A1 | 5/2002 | Scott et al. |
| 2002/0095197 A1 | 7/2002 | Lardo et al. |
| 2002/0097050 A1 | 7/2002 | Kellman et al. |
| 2002/0161421 A1 | 10/2002 | Lee et al. |
| 2002/0167315 A1 | 11/2002 | Kellman et al. |
| 2002/0177771 A1 | 11/2002 | Guttman et al. |
| 2002/0192688 A1 | 12/2002 | Yang et al. |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0199755 A1 | 10/2003 | Halperin |
| 2004/0015079 A1 | 1/2004 | Berger et al. |
| 2004/0024434 A1 | 2/2004 | Yang et al. |
| 2004/0046557 A1 | 3/2004 | Karmarkar et al. |
| 2004/0167392 A1 | 8/2004 | Halperin et al. |
| 2004/0263173 A1 | 12/2004 | Gray |
| 2004/0263174 A1 | 12/2004 | Gray et al. |
| 2005/0197677 A1 | 9/2005 | Stevenson |
| 2006/0009819 A1 | 1/2006 | Przybyszewski |
| 2006/0247684 A1 | 11/2006 | Halperin et al. |
| 2006/0259093 A1 | 11/2006 | Stevenson et al. |
| 2007/0088416 A1 | 4/2007 | Atalar et al. |
| 2008/0058635 A1 | 3/2008 | Halperin et al. |

FOREIGN PATENT DOCUMENTS

| | | |
|---|---|---|
| EP | 0 145 430 B1 | 5/1991 |
| EP | 0 466 424 | 1/1992 |
| EP | 466 424 | 1/1992 |
| EP | 557 127 | 8/1993 |
| EP | 0 673 621 | 9/1995 |
| EP | 0 673 621 A1 | 9/1996 |
| EP | 0 498 996 B1 | 3/1997 |
| EP | 1 021 730 B1 | 4/2003 |
| EP | 0 930 509 B1 | 3/2004 |
| JP | 60141034 | 7/1985 |
| JP | 61181925 | 8/1986 |
| JP | 62233905 | 10/1987 |
| JP | 4071536 | 3/1992 |
| JP | 6-70902 | 3/1994 |
| JP | 6 70902 | 3/1994 |
| JP | 6054823 | 3/1994 |
| JP | 9-94238 | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/29685 | 8/1997 |
| WO | 97/29710 | 8/1997 |
| WO | WO 97/40396 | 10/1997 |
| WO | WO 98/52461 | 11/1998 |
| WO | WO 99/19739 | 4/1999 |
| WO | WO 00/10456 | 3/2000 |
| WO | WO 00/25672 | 5/2000 |
| WO | WO 02/083016 | 10/2002 |
| WO | WO 2006/031317 A2 | 3/2006 |

OTHER PUBLICATIONS

Dumoulin et al, "Real-Time Position Monitorng of Invasive Devices Using Magnetic Resonance", MRM 29:411-415 (1993).

Bauernfeind et al., "Chronic Nonparoxysmal Sinus Tachycardia in Otherwise Healthy Persons", Ann. Intern. Med. 91: 702-710 (1979).

Chen et al., "Right Atrial Focal Atrial Fibrillation: Electrophysiologic Characteristics and Radiofrequency Catheter Ablation," J. Cardiovasc. Electrophysiol. 10: 328-335 (1999).

Chorro et al., "Transcatheter Ablation of the Sinus Node in Dogs Using High-Frequency Current", European Heart J. 11: 82-89 (1990).

Cox et al., "Modification of the Maze Procedure for Atrial Flutter and Atrial Fibrillation, II: Surgical Technique of the Maze III Procedure", J. Thorac. Cardiovasc. Surg. 110: 485-495 (1995).

Edelman et al., "Magentic Resonance Imaging," NEJM, 328: 708-716 (1993).

Garrey, W.E., "The Nature of Fibrillary Contraction of the Heart—Its Relation to Tissues Mass and Form," Am. J. Physiol., 33: 397-414 (1914).

Garwood et al., "Magnetic Resonance Imaging With Adiabatic Pulses Using a Single Surface Coil for RF Transmission and Signal Detection", Magnetic Resonance in Medicine, 9: 25-34 (1989).

Haines et al., Primary Atrial Fibrillation Ablation (PAFA) in a chronic Atrial Fibrillation Model, Circulation, 92(8): I-265(#1261) (1995).

Haissaguerre et al., "Spontaneous Initiation of Atrial Fibrillation by Ectopic Beats Orginiating in the Pulmonary Veins", New Engl. J. Med. 339: 659-666 (1998).

D.I. Hoult et al, "The Signal-To-Noise Ratio of the Nuclear Magnetic Resonance Experiment", Journal of Magnetic Resonance, 24: 71-85 (1976).

D.I. Hoult, "Rotating Frame Zeugmatography", Phil. Trans. R. Soc. Lond. B., 289, 543-547 (1980).

Hsieh et al., "Double Multielectrode Mapping Catheters Facilitate Radiofrequency Catheter Ablation of Focal Atrial Fibrillation Originating From Pulmonary Veins", J. Cardio-Vasc. Electrophysiol. 10: 136-144 (1999).

Jais et al., "A Focal Source of Atrial Fibrillation Treated by Discrete Radiofrequency Ablation", Circulation, 95:572-576 (1997).

Ferenc Jolesz et al., "Inverventional Magnetic Resonance Therapy", Seminars in Interventional Radiology, vol. 12, No. 1: 20-27 (1995).

Jonathan Kalman et al., Biophysical Characteristics of Radiofrequency Lesion Formation in Vivo: Dynamics of Catheter Tip-Tissue Contact Evlauated by Intracardiac Echocardiography, Am. Heart J. 133(1), 8-18 (1997).

Jonathan Kalman et al, "Cristal Tachycardia—Relationship of Right Atrial Tachycardias to the Crista Terminalis Identified Using Intracardiac Echocardiography", Pacing and Clinical Electrophysiology, 18, 261 (1995).

Jonathan Kalman et al., "Radiofrequency Catheter Modification of Sinus Pacemaker Function Guided by Intracardiac Echocardiography", Circulation, 3070-3081 (1995).

G. Neal Kay et al,. "Radiofrequency Ablation for Treatment of Primaery Atrial Tachycardias", JACC vol. 21, No. 4, 901-909 (1993).

Michael Lee et al., "Catheter Modification of the Atrioventricular Junction With Radiofrequency Energy for Control of Atrioventricular Nodal Reentry Tachycardia", Circulation 83, 827-835 (1991).

Michael Lesh et al., "Radiofrequency Catheter Ablation of Atrial Arrhythmias", Circulation 89, 1074-1089 (1994).

Mark Mitchell et al., "Morphologic and {Physiologic Characteristics of Discontinuous Linear Atrial Ablations During Atrial Pacing and Atrial Fibrillation", Pace, 20 vol. 20 (Part II), 202 (1997).

G.K. Moe et al., "Atrial Fibrillation As a Self-Sustaining Arrhythmia Independent of Focal Discharge", American Heart Jornal, 58, 59-70 (1959).

G.K. Moe et al., "On the Multiple Wavelet Hypothesis of Atrial Fibrillation", Arch. Int. Pharmacodyn. Ther. 140, 183-199 (1962).

Andrea Natale et al., "Catheter Ablation Approach on the Right Side Only for Paroxysmal Atrial Fibrillation Therapy", Circulation, 1-266 (#1265) vol. 92, No. 8 (1995).

Ogan Ocali et al., "Intravascular Magnetic Resonance Imaging Using a Loopless Catheter Antenna", MRM, 37, 112-118 (1997).

Eric Prystowsky et al., "Management of Patients With Atrial Fibrillation: A Statement for Healthcare Professionals From the Subcommittee on Electrocardiography and Electrophysiology, American Heart Association", Circulation 93, 1262-1277 (1966).

Stuart Silverman et al., "Interactive MR-guided Biopsy in an Open-Configuration MR Imaging System", Radiology, 197, 175-181 (1995).

John Swartz et al., "A Catheter-Based Curative Approach to Atrial Fibrillation in Humans", Abstracts From the 67$^{th}$ Scientific Sessions, 1-335: 1794 (1994).

Cynthia Tracy et al., "Radiofrequency Catheter Ablation of Ectopic Atrial Tachycardia Using Paced Activation Sequence Mapping", JACC vol. 21, No. 4, 910-917 (1993).

Theodore West et al., "Miminal Mass Required for Induction of a Sustained Arrhythmia in Isolated Atrial Segments", Am. J. Physiol., 202, 232-236 (1962).

Bernard Zimmermann et al., "Artifacts and Hazards in NMR Imaging Due to Metal Implants and Cardiac Pacemakers", Diagn. Imag. Clin. Med. 53, 53-56 (1984).

Douglas Zipes, "Atrial Fibrillation: A Tachycardia-Induced Atrial Cardiomyopathy", Circulation 95, 562-564 (1997).

P.V. Karmarkar et al., "An Active MRI Intramyocardial Injection Catheter", Proc. Intl. Soc. Mag. Reson. Med, 11, 311 (2003).

Ananda Kumar, "MR Imaging With a Biopsy Needle", Proc. Intl. Soc. Mag. Reson. Med. 9, 2148 (2001).

Robert C. Susil et al., "Multifunctional Interventional Devices for MRI: A Combined Electrophysiology/MRI Catheter", Mag. Reson. Med., 47, 594-600 (2002).

H.H. Quick et al., "Endourethral MRIi", Intl. Soc. Mag. Reson. Med., 1, 142 (2000).

International Search Report, PCT Application No. PCT/US/03/17085, mailed Sep. 29, 2003.

Ariel Roguin, et al., "Modern Pacemaker and Implantable Cardioverter/Defibrillator Systems Can Be Magnetic Resonance Imaging Safe: in Vitro and In Vivo Assessment of Safety and Function at 1.5 T," American Heart Association, Circulation—Journal of the American Heart Association, 475-482, Dallas, Texas, USA (Aug. 3, 2004, originally published online Jul. 26, 2004).

C. Gabriel, S. Gabriel and E. Corthout, "The Dielectric Properties of Biological Tissues: I. Literature Survey," Phys. Med. Biol. 41:2231-2249 (1996).

Garrey, Walter E., "The Nature of Fibrillary Contraction of the Heart—Its Relation to Tissue Mass and Form," Am. J. Physiol. 33:397-414 (1914).

Robert C. Susil, Ergin Atalar, Albert Lardo, "Multifunctional Interventional Devices for Use in MRI," U.S. Appl. No. 60/283,725, filed Apr. 13, 2001.

Roger Christoph Luchinger, "Safety Aspects of Cardiac Pacemakers in Magnetic Resonance Imaging," a dissertation submitted to the Swiss Federal Institute of Technology Zurich, Zurich, Switzerland (2002).

S. Gabriel, R.W. Lau and C. Gabriel, "The Dielectric Properties of Biological Tissues: II. Measurements in the Frequency Range 10 Hz to 20 GHz," Phys. Med. Biol. 41:2251-2269 (1996).

Official Communication, U.S. Appl. No. 11/932,227, mailed May 20, 2010 (15 pages).

Atalar et al., "High Resolution Intravascular MRI and MRS using a Catheter Receiver Coil," Magnetic Resonance in Medicine, 36:596-605 (1996).

SYSTEM AND METHOD FOR MAGNETIC-RESONANCE-GUIDED ELECTROPHYSIOLOGIC AND ABLATION PROCEDURES

RELATED APPLICATION

This application is a continuation of U.S. patent application Ser. No. 10/424,093, filed Apr. 28, 2003 now U.S. Pat. No. 7,155,271, which is a divisional application of U.S. patent application Ser. No. 09/428,990 (U.S. Pat. No. 6,701, 176) filed Oct. 29, 1999, and claims the benefit of U.S. Provisional Patent Application No. 60/106,965 filed Nov. 4, 1998, the entire contents of all of which are incorporated herein by reference.

BACKGROUND OF THE INVENTION

1. Field of the Invention

The invention relates in general to ablation and electrophysiologic diagnostic and therapeutic procedures, and in particular to systems and methods for guiding and providing visualization during such procedures.

2. Related Art

Atrial fibrillation and ventricular tachyarrhythmias occurring in patients with structurally abnormal hearts are of great concern in contemporary cardiology. They represent the most frequently encountered tachycardias, account for the most morbidity and mortality, and, despite much progress, remain therapeutic challenges.

Atrial fibrillation affects a larger population than ventricular tachyarrhythmias, with a prevalence of approximately 0.5% in patients 50-59 years old, incrementing to 8.8% in patents in their 80's. Framingham data indicate that the age-adjusted prevalence has increased substantially over the last 30 years, with over—2 million people in the United States affected. Atrial fibrillation usually accompanies disorders such as coronary heart disease, cardiomyopathies, and the postoperative state, but occurs in the absence of any recognized abnormality in 10% of cases. Although it may not carry the inherent lethality of a ventricular tachyarrhythmia, it does have a mortality twice that of control subjects. Symptoms which occur during atrial fibrillation result from the often rapid irregular heart rate and the loss of atrio-ventricular (AV) synchrony. These symptoms, side effects of drugs, and most importantly, thromboembolic complications in the brain (leading to approximately 75,000 strokes per year), make atrial fibrillation a formidable challenge.

Two strategies have been used for medically managing patients with atrial fibrillations. The first involves rate control and anticoagulation, and the second involves attempts to restore and maintain sinus rhythm. The optimal approach is uncertain. In the majority of patients, attempts are made to restore sinus rhythm with electrical or pharmacologic cardioversion. Current data suggest anticoagulation is needed for 3 to 4 weeks prior to and 2 to 4 weeks following cardioversion to prevent embolization associated with the cardioversion. It remains controversial whether chronic antiarrhythmic therapy should be used once sinus rhythm is restored. Overall, pharmacologic, therapy is successful in maintaining sinus rhythm in 30 to 50% of patients over one to two years of follow-up. A major disadvantage of antiarrhythmic therapy is the induction of sustained, and sometimes lethal, arrhythmias (proarrhythmia) in up to 10% of patients.

If sinus rhythm cannot be maintained, several approaches are used to control the ventricular response to atrial fibrillation. Pharmacologic agents which slow conduction through the AV node are first tried. When pharmacologic approaches to rate control fail, or result in significant side effects, ablation of the AV node, and placement of a permanent pacemaker is sometimes considered. The substantial incidence of thromboembolic strokes makes chronic anticoagulation important, but bleeding complications are not unusual, and anticoagulation cannot be used in all patients.

Medical management of atrial fibrillation, therefore, is inadequate.

In addition to medical management approaches, surgical therapy of atrial fibrillation has also been performed. The surgical-maze procedure, developed by Cox, is an approach for suppressing atrial fibrillation while maintaining atrial functions.

This procedure involves creating multiple linear incisions in the left and night atria.

These surgical incisions create lines of conduction block which compartmentalize the atrium into distinct segments that remain in communication with the sinus node. By reducing the mass of atrial tissue in each segment, a sufficient mass of atrial tissue no longer exists to sustain the multiple reentrant rotors, which are the basis for atrial fibrillation. Surgical approaches to the treatment of atrial fibrillation result in an efficacy of >95% and a low incidence of complications. Despite these encouraging results, this procedure has not gained widespread acceptance because of the long duration of recovery and risks associated with cardiac surgery.

Invasive studies of the electrical activities of the heart (electrophysiologic studies) have also been used in the diagnosis and therapy of arrhythmias, and many arrhythmias can be cured by selective destruction of critical electrical pathways with radio-frequency (RF) catheter ablation. Recently, electrophysiologists have attempted to replicate the maze procedure using radio-frequency catheter ablation, where healing destroys myocardium. The procedure is arduous, requiring general anesthesia and procedure durations often greater than 12 hours, with exposure to x-rays for over 2 hours. Some patients have sustained cerebrovascular accidents.

One of the main limitations of the procedure is the difficulty associated with creating and confirming the presence of continuous linear lesions in the atrium. If the linear lesions have gaps, then activation can pass through the gap and complete a reentrant circuit, thereby sustaining atrial fibrillation or flutter. This difficulty contributes significantly to the long procedure durations discussed above.

Creating and confirming continuous linear lesions could be facilitated by improved techniques for imaging lesions created in the atria. Such an imaging technique may allow the procedure to be based purely on anatomic findings.

The major technology for guiding placement of a catheter is x-ray fluoroscopy. For electrophysiologic studies and ablation, frame rates of 7-15/sec are generally used which allows an operator to see x-ray-derived shadows of the catheters inside the body. Since x-rays traverse the body from one side to the other, all of the structures that are traversed by the x-ray beam contribute to the image. The image, therefore is a superposition of shadows from the entire thickness of the body. Using one projection, therefore, it is only possible to know the position of the catheter perpendicular to the direction of the beam. In order to gain information about the position of the catheter parallel to the beam, it is necessary to use a second beam that is offset at some angle from the original beam, or to move the original beam to another angular position. Since x-ray shadows are the superposition of contributions from many structures, and since the discrimination of different soft tissues is not great, it is often very difficult to determine exactly where the catheter is within the heart. In addition, the boarders of the heart are generally not accurately defined, so it is generally not possible to know if the catheter has penetrated the wall of the heart.

Intracardiac ultrasound has been used to overcome deficiencies in identifying soft tissue structures. With ultrasound it is possible to determine exactly where the walls of the heart are with respect to a catheter and the ultrasound probe, but the ultrasound probe is mobile, so there can be doubt where the absolute position of the probe is with respect to the heart. Neither x-ray fluoroscopy nor intracardiac ultrasound have the ability to accurately and reproducibly identify areas of the heart that have been ablated.

A system known as "non-fluoroscopic electroanatomic mapping (Ben-haim; U.S. Pat. No. [5,391,199),] was developed to allow more accurate positioning of catheters within the heart. That system uses weak magnetic fields and a calibrated magnetic field detector to track the location of a catheter in 3-space. The system can mark the position of a catheter, but the system relies on having the heart not moving with respect to a marker on the body. The system does not obviate the need for initial placement using x-ray fluoroscopy, and cannot directly image ablated tissue.

MR is a known imaging technique which uses high-strength magnetic and electric fields to image the body. A strong static magnetic field (between the magnet poles in this example) orients the magnetic moments of the hydrogen nuclei. RF time-varying magnetic field pulses change the spatial orientation of the magnetic moments of the nuclei. To exert a significant torque on the moment, the frequency of the magnetic field must be equal to the frequency of precession of the magnetic moment of the nuclei about the direction of the static magnetic field. This frequency of precession is a natural, or resonance, frequency of the system (hence Magnetic Resonance Imaging).

The time-varying gradient magnetic field is used for spatial encoding of the signals from the issue. The magnitude of the gradient field is a linear function of the space coordinates in the magnet. As a result of the addition of the static and gradient magnetic fields, the total local magnetic field and, thus, the local resonance frequency, becomes a linear function of position. Thus, imaging tissues in any plane can be accomplished because the location of each volume element is known in three-dimensional space.

MRI is generally considered a safe technique, since no x-rays are used and the electromagnetic fields do not, by themselves, cause tissue damage.

While MRI may provide the visual guidance necessary for creating and confirming linear lesions, it has been assumed that electrical wires implanted in a patient can act as antennas to pick up radio-frequency energy in an MR system and conduct that energy to the patient, thereby causing tissue injury.

Magnetic resonance imaging has been used to guide procedures in which RF energy is applied to non-contractile organs such as the brain, liver and kidneys to ablate tumors. However, these systems are not suitable for use in the heart.

U.S. Pat. No. 5,323,778 to Kandarpa et al. discloses a method and apparatus for magnetic resonance imaging and tissue heating. There is no provision in the disclosed probe for measuring electrical signals; and, it is unclear how much resolution the probe provides.

OBJECTS AND SUMMARY OF THE INVENTION

It is therefore an object of the invention to provide an improved system and method for guiding and/or providing visualization during electrophysiologic procedures.

It is a further object of the invention to provide a system and method for guiding or visualizing ablation procedures which is suitable for use in the heart and other structures.

It is a further object of the invention to provide a system and method for imaging ablation lesions with increased resolution and reliability.

The invention provides a system and method for using magnetic resonance imaging to increase the safety and accuracy of electrophysiologic procedures. The system in its preferred embodiment provides an invasive combined electrophysiology and imaging antenna catheter which includes an RF antenna for receiving magnetic resonance signals and diagnostic electrodes for receiving electrical potentials. The combined electrophysiology and imaging antenna catheter is used in combination with a magnetic resonance imaging scanner to guide and provide visualization during electrophysiologic diagnostic or therapeutic procedures. The invention is particularly applicable to catheter ablation of atrial and ventricular arrhythmias. In embodiments which are useful for catheter ablation, the combined electrophysiology and imaging antenna catheter may further include an ablation tip, and such embodiment may be used as an intracardiac device to both deliver energy to selected areas of tissue and visualize the resulting ablation lesions, thereby greatly simplifying production of continuous linear lesions. Additionally, the ablation electrode can be used as an active tracking device that receives signal from the body coil excitation. Gradient echoes are then generated along three orthogonal axes to frequency encode the location of the coil and thus provide the three-dimensional space coordinates of the electrode tip. These numeric coordinates can then be used to control the imaging plane of the scanner, thereby allowing accurate imaging slices to be automatically prescribed though the anatomic target for RF therapy. The invention further includes embodiments useful for guiding electrophysiologic diagnostic and therapeutic procedures other than ablation. Imaging of ablation lesions may be further enhanced by use of MR contrast agents. The antenna utilized in the combined electrophysiology and imaging catheter for receiving MR signals is preferably of the coaxial or "loopless" type that utilizes a helical whip.

High-resolution images from the antenna may be combined with low-resolution images from surface coils of the MR scanner to produce a composite image. The invention further provides a system for eliminating the pickup of RF energy in which intracardiac wires are detuned, by for example low-pass filters, so that they become very inefficient antennas. An RF filtering system is provided for suppressing the MR imaging signal while not attenuating the RF ablative current. Steering means may be provided for steering the invasive catheter under MR guidance. Lastly, the invention provides a method and system for acquisition of high-density electroanatomic data using a specially designed multi-electrode catheter and the MRI scanner. This will be achieved by using an active tracking system that allows the location of each electrode to be determined.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

The invention in its preferred embodiment uses MR imaging to allow catheters to be placed without radiation, and provides very accurate localization of catheter tips in 3-dimensional space. With current MRI scanners, resolution is limited by the distance the RF coil is from the volume of tissue being imaged. RF from any particular imaging volume is picked up by the surface coil. The gradients select a volume inside the body for imaging, but the coil outside the body picks up the signal from the volume. The farther the surface coil is from the imaging volume, the more noise will be present.

In accordance with a preferred embodiment of the invention, an intracardiac receiving coil/antenna is used so that the receiving coil/antenna is closer to the imaging volume (lesions), thereby reducing noise, increasing signal, and improving resolution where it is needed most.

In a first embodiment of the invention, MRI is used to facilitate catheter ablation of atrial fibrillation by guiding creation of continuous linear ablation lesions and confirming that a complete linear lesion has been created (line of block). The visualization of areas of ablation may allow a reduction in the number of lesions needed, and may also reduce the number of recurrences, by more accurately ablating the arrhythmias.

Figure 1:
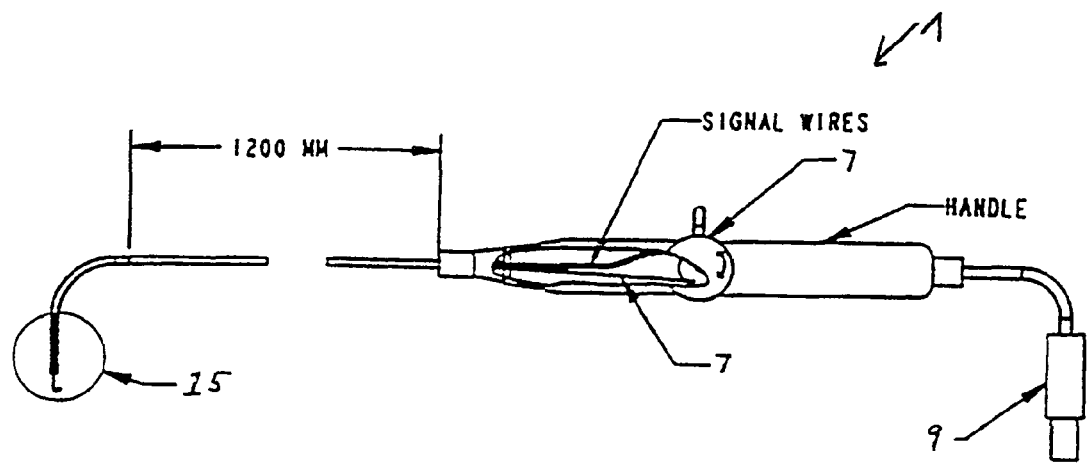
FIG. 1 shows a schematic view of a combined electrophysiology and imaging antenna catheter in accordance with a preferred embodiment of the invention.
Figure 2:
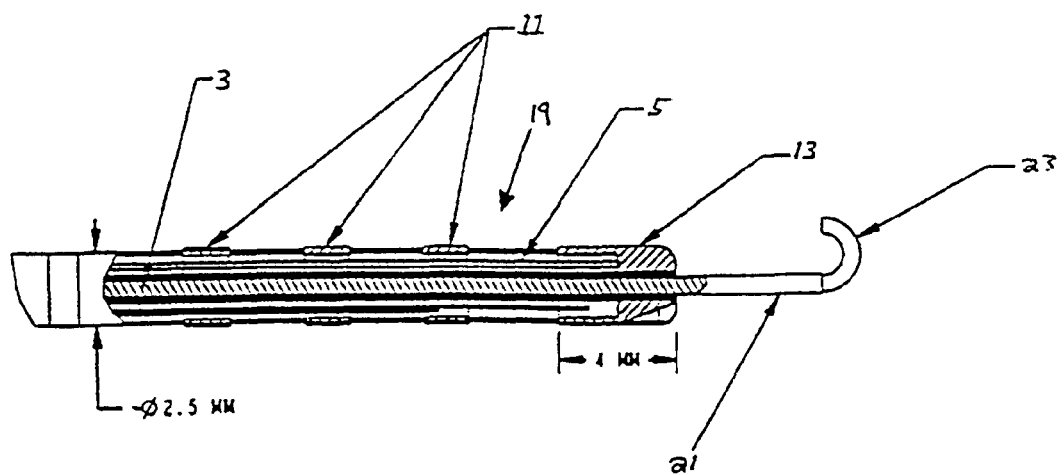
FIG. 2 shows a cross-sectional detail view of a tip portion of combined electrophysiology and imaging antenna catheter in accordance with a preferred embodiment of the invention.

FIGS. 1 and 2 show schematic and detail views, respectively, of a combined electrophysiology and imaging antenna catheter in accordance with a preferred embodiment of the invention. The device of the invention is used in combination with an MRI scanner such that RF energy can be delivered to selected areas of tissue, the tissue imaged with an invasive (e.g., intracardiac) antenna, and RF lesions or other targets can be visualized in both high and low resolution modes. MRI allows visualization of lesions in the ventricle with the use of surface coils, and in the atria with surface coils and/or the intracardiac catheter-antenna. With these catheter antennae, the image can be aligned perpendicular to the catheter, such that the best resolution will be at site of the lesion. This lesion visualization can be used for (1) precise titration of therapy, (2) the ability to test the length and depth of lesions from new ablation-energy sources, and (3) accurate assessment of the success of making lines of ablation.

In addition to catheter-antenna, high-resolution imaging can also be done with receivers that contain loops that are placed inside the body. These loops may be fixed in size or may be expandable once placed in the body to increase their surface area.

MRI can also be used in accordance with the invention to guide other procedures.

In cardiology, accurate anatomic information, combined with electrical measurements, allows improved study of the pathophysiology of arrhythmias, stunning, remodeling, and tachycardia-induced myopathy. Outside of cardiology, it has already been demonstrated that biopsies of liver, kidney, adrenal gland, neck masses, and lymph nodes could all be done safely and accurately with MR-guidance. With extensions of the biopsy technique, MRI-guided ablation of tumors such as metastatic liver disease, brain tumors, and prostate cancer, may allow treatment with less morbidity and less cost than conventional open surgery.

FIG. 1 shows a schematic diagram of the device 1 of the invention and FIG. 2 shows a detail view of a tip portion 15 of the device. The system of the invention preferably comprises a combined electrophysiology and imaging antenna catheter 1 which is used in conjunction with an MRI scanner such that visualization can be performed simultaneously with delivery of RF energy to selected areas of tissue for ablation. In embodiments designed for cardiac ablation applications, the length of the invasive portion of the device is preferably at least 1200 millimeters long so that the tip can be placed into the heart from the femoral artery or vein. The diameter of the device is approximately 2.5 mm.

The device preferably includes between one and three diagnostic electrodes 11 for receiving electrical potentials, e.g., intracardiac potentials, in connection with electrophysiological procedures and testing. In embodiments useful for ablation applications, the device further includes an ablation tip 13. The electrodes 11 are preferably fabricated from platinum or gold. The tip portion 15 of the device is deflectable by a steering wire 5, preferably of titanium construction, that is inside a low-friction sheath, preferably of Teflon construction. The steering wire 5 connects to a steering knob 7 and moves toward or away from the tip when the steering knob 7 is rotated, deflecting the tip in the appropriate direction. A connector 9 is used to interconnect the antenna 3 with receiver or scanner circuitry, which is discussed in further detail below, and is also used to connect the electrodes 11 to external electronic devices.

The device of the invention includes an antenna portion 19, which may be of various suitable designs. In the preferred embodiment, a flexible, helical whip coaxial loopless antenna is used. Such an antenna can be made by removing a section of the shield from an antenna coaxial cable, so as to form a 'whip' with the center conductor.

To avoid direct biofluid contact with conductive components of the catheter it will be covered with a non-conductive dielectric material. Addition of insulation to the antenna, however, increases the whip length required for optimal image quality to a length that prohibitively large for in vivo use. Incorporating a helical whip in the loopless antenna design overcomes this limitation by allowing up to 10 times the electrical length to be achieved in the same physical length as a straight conductor whip. In addition to these electromagnetic advantages, the helical antenna whip also improves the mechanical properties of the device and thereby greatly improve intravascular and intracardiac navigation of the catheter without kinking, folding or mechanical failure of the whip. The flexible helical whip has guidewire properties and thus reduces the risks of vascular or cardiac perforation. The length of helical whip can be varied to help in tuning the antenna to the optimal impedance and in optimizing the signal-to-noise ratio. Further details regarding the structure and design of suitable loopless antennas can be found in U.S. Pat. No. 5,928,145, issued Jul. 27, 1999, the entire disclosure of which is incorporated herein by reference.

Since loops can receive more signal in a given imaging volume, an antenna incorporating a loop may provide an improved signal-to-noise ratio, resulting in clearer images. A loop can be formed, where the antenna whip 21 is connected to the antenna body 19 via a miniature capacitor. A balloon can be incorporated into the catheter, and the loop can be attached to the surface of the balloon. When the balloon is inflated, the loop will expand.

In embodiments of the invention wherein a coaxial loopless antenna is utilized, a helical whip portion 21 of the flexible antenna protrudes from the distal tip to complete the dipole antenna. The whip portion 21 is coated with an insulating layer and its tip 23 can be exposed and formed into a "J" to help prevent the whip from perforating internal physiological structures. The antenna whip portion 21 should be insulated from the ablation tip.

When the device of the invention is used for intracardiac ablation procedures, tissue is imaged with the antenna and RF lesions can be visualized in both high and low resolution modes. As is discussed in detail below, the images may be enhanced with MRI contrast, such as gadolinium. Software can be provided for optimally visualizing the lesions, and for allowing the operator to change viewing perspective in near-real time.

As is set forth above, embodiments of the invention which are useful for ablation procedures preferably include an ablation tip 13. As an alternative to the preferred embodiment wherein the active element of the antenna runs within the catheter in a coaxial fashion, the RF ablation element in the ablation tip may be designed to serve both as an RF ablation transmitter and as a receiver coil for MR imaging. In such embodiments, a switching device can be used to switch the catheter between imaging and ablation modes. When not in ablation mode, the ablation electrode, and the other electrodes on the catheter, can be used to measure electrical signals.

Another embodiment of the combined antenna and RF probe device is the use of untuned RF electrodes as tracking devices. Single or multiple RF electrodes may serve as small RF coils that receive signal from the body coil excitation and then are frequency encoded in three orthogonal planes. These three space numeric coordinates can then be used to automatically control the imaging plane of the scanner, allowing optimal imaging of the target region for RF therapy. Additionally, as the electrodes can also acquire bioelectric signals, electrode location data allows the generation of true electroanatomic data.

For most applications, the impedance of the imaging antenna must match the impedance of the input amplifier. With an ordinary 64 MHz input amplifier, this impedance is 50 Ohms. A number of matching networks are possible, the simplest being a series capacitor of an appropriate value. A network analyzer can be used to allow optimal matching of different antenna designs. o customize matching to an individual patient, the network analyzer can be automated and incorporated into the matching network to automatically tune the matching network after the antenna has been placed into the patient.

The catheter antenna device of the invention in accordance with its preferred embodiment is constructed so as to be fully MRI-compatible. Specifically, it's design and materials are selected such that (1) the image is not significantly distorted by the device; (2) the MRI electromagnetic fields do not alter the normal functioning of the device; (3) cardiac arrhythmias are not produced by the device, and (4) no damage to the tissue is produced by radio-frequency energy received from the MRI scanner. The presence of even small amounts of magnetic material in the imaging fields can produce substantial amounts of image distortion. This distortion is caused by perturbation of the imaging magnetic field. The most distortion is caused by ferromagnetic materials (iron, nickel, cobalt). Little if any distortion is produced by materials that do not become significantly magnetized (low magnetic susceptibility) by the MRI magnetic field. Metals which do not produce significant magnetization include copper, gold, platinum and aluminum. Many plastics and synthetic fibers are entirely non-magnetic and do not distort the images.

Figure 3:
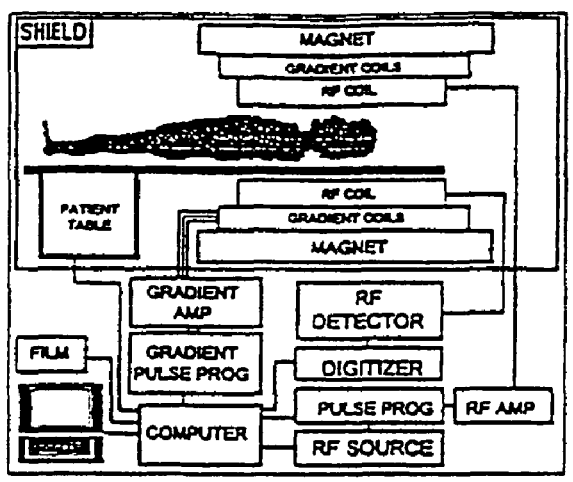
FIG. 3 shows a block diagram illustrating the operation of an MRI scanner system which may be used in connection with the system and method of the invention.

FIG. 3 shows a block diagram illustrating the operation of an MRI scanner system which may be used in connection with the system and method of the invention.

A magnet is provided for creating the magnetic field necessary for inducing magnetic resonance. Within the magnet are gradient coils for producing a gradient in the static magnetic field in three orthogonal directions. Within the gradient coils is an RF coil.

The RF coil produces the magnetic field necessary to rotate the spins of the protons by 90° or 180°. The RF coil also detects the signal from the spins within the body. A computer is provided for controlling all components in the imager. The RF components under control of the computer are the RF frequency source and pulse programmer. The source produces a sine wave of the desired frequency. The pulse programmer shapes the RF pulses, and the RF amplifier increases the pulse power up to the kilo-watt range. The computer also controls the gradient pulse programmer which sets the shape and amplitude of each of the three gradient fields. The gradient amplifier increases the power of the gradient pulses to a level sufficient to drive the gradient coils.

Figure 4:
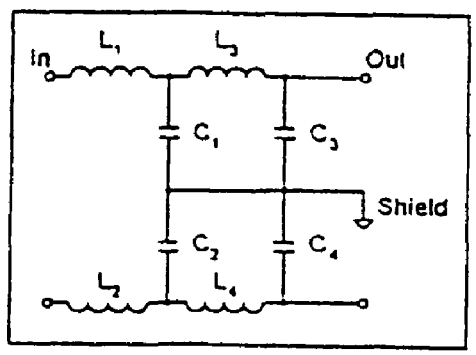
FIG. 4 illustrates a schematic block diagram showing an example of radio-frequency filters which may be used in accordance with the invention.

The invention in accordance with a preferred embodiment further includes filter means and shielding for protecting electronic equipment (e.g., the MR scanner) from RF produced by the ablation system, for protecting the ablation and measuring system from RF produced by the MR scanner, and for allowing measurement of the relevant electrical signals. Without adequate radio-frequency filters, the electronics attached to the catheter may malfunction during imaging. FIG. 4 illustrates a schematic block diagram showing an example of radio-frequency filters which may be used in accordance with the invention. Low-pass filters using 1-henry inductors made without magnetic materials, and 220 picofarad capacitors, have optimal attenuation of the 64 Mhz radio-frequency energy present in the 1.5 Tesla MR scanner. A number of filter topologies were tested, and the two stage filter shown in FIG. 4 had the best results. A separate two-stage filter (Li, L3, C1, C3; and L2, L4, C2, C4), is preferably placed in each wire to the catheter. These filters can reduce the 15-32 volts of radio-frequency pickup down to a few millivolts and cause no problems with the electronics.

The output of the RF filters can be applied to a series of active filters. The active filters may comprise, e.g., a sixth order, Chebyshev (1 dB ripple), low-pass filter (50-300 Hz corner); then a second order, Chebyshev (1 dB ripple), high-pass filter (3-50 Hz corner); and then a 60 Hz notch filter. These filters limit the signal bandwidth, and substantially reduce gradient-field-induced noise—see FIG. 5(c), discussed below. The gradient field noise was not rejected by the RF filters. This filter arrangement is used in the catheter-intracardiac electrogram measuring circuit. The circuit for ablation does not incorporate the active filters, since while the RF filtering system is designed to suppress the 64 MHz imaging signal. It does not attenuate the RF ablative current, since the radio frequency of the ablation system is 200-800 kHz, and the corner for the low- pass RF filters is 1-10 MHz. The ablation circuit does not need the lower-frequency filters, since that circuit is not being used to measure electrograms.

Figure 5:
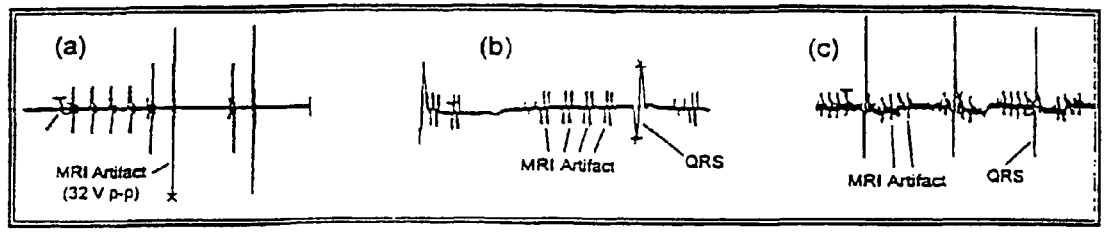
FIG. 5 shows a graphic representation of electrical signals measured from a catheter in accordance with the invention during MR imaging.

FIG. 5 shows a graphic representation of electrical signals measured from a catheter in accordance with the invention during MR imaging. FIG. 5(a) shows the signals measured from a catheter without the use of RF filters; it can be seen that the ECG is obscured by noise (32 volts peak-to-peak). FIG. 5(b) shows such signals wherein RF filters are used; it can be seen that nearly all radio-frequency interference is removed and an ECG signal is now apparent. The pairs of vertical lines are artifacts from the gradient fields. FIG. 5(c) shows such signals wherein active RF filters are used; it can be seen that most of the gradient artifact is also suppressed.

Figure 6:
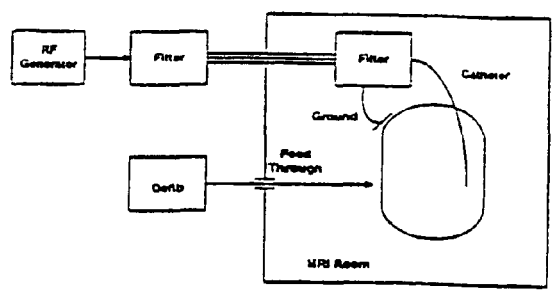
FIG. 6 shows a high-level block diagram illustrating an ablation system incorporating radio-frequency filters in accordance with a preferred embodiment of the invention.

FIG. 6 shows a high-level block diagram illustrating an ablation system incorporating the filters described above. The RF Generator may comprise, e.g., a standard clinically approved ablation unit, such as those commercially available from Medtronic, having an RF output frequency of 482.6 5 kHz and an output of 50 W into a 50-250 Q load. The output frequency from the RF generator is directed to the ablation catheter through two filter assemblies (low pass, 2 Mhz corner). Both filter assemblies are fully shielded and are connected by fully shielded cable. The ECG amplifiers incorporate the active filters as described above. The dispersive ground electrode consists of a large conductive-adhesive pad that is attached to the skin of the animal to complete the circuit. The defibrillator (identified as "defib" in FIG. 8) may comprise a standard defibrillator used in ablation procedures.

It is important that the location of the tip of the catheter can be accurately determined. A number of modes of localization can be used. Because the catheter is a receiver it can be used to directly image the tissue around it. This image can be viewed on its own at high resolution, or, it can be viewed at low resolution as an overlay on a large field-of-view "scout" image obtained with an auxiliary coil outside the body. The location of the catheter in the body can be tracked by the bright line of signal moving in the scout image. The scout image can be updated at an interval set by the user to compensate for patient motion. An interactive control will allow the physician to "zoom in" towards the bright catheter, finally resulting in a high resolution image around the catheter tip. The "zoom" function can be achieved with interactive control of the imaging gradients.

A composite "medium resolution" resolution image can be used to construct a three-dimensional map of the areas in the heart that have undergone ablation. These areas will be marked by elevated T2 values, or decreased T1 values during Gd infusion.

A composite three-dimensional rendering of the heart can be updated after each ablation and displayed with an appropriate rendering technique.

The guidance of the catheter tip to the next site of ablation, or to fill in a previous ablation line can be assisted using the MR images. This assistance can be entirely passive, in that the physician uses the images to manipulate the catheter, or automatic tracking and feedback could assist that physician to steer the catheter.

The lesions may be visualized using standard imaging techniques. It may be necessary to MR contrast to enhance the lesions to allow adequate visualization to occur. One such enhancement method uses gadolinium-DTPA, but other suitable contrast agent could be used. The rationale underlying the utilization of gadolinium-DTPA based contrast agents to enhance signal intensity in atrial or ventricular myocardium injured by RF during therapeutic ablation is based on the following observations: 1) Gadolinium-DTPA exerts its signal enhancing effect by interacting with water protons and inducing a shorter relaxation time in response to any given radio-frequency stimulus. This effect creates the image contrast necessary to allow distinction in relation to regions unaffected by contrast. 2) Gadolinium-DTPA is a large molecule which cannot penetrate the uninjured cell membrane and is therefore restricted to the extracellular space in uninjured myocardium. After the RF burn, the injured membrane allows penetration of the contrast agent thus increasing significantly the volume of distribution for the contrast agent and resulting in a 'brighter' voxel of tissue on T1 weighted images. 3) This difference in voxel content of water protons potentially exposed to the gadolinium-DTPA molecule creates the possibility of distinguishing injured from non-injured tissue with greater spatial resolution than in non-enhanced images.

Gadolinium-DTPA can be injected prior to the RF ablation protocol to enhance injured myocardium as the lesions are produced. The agent takes 5-10 minutes to equilibrate between extracellular and intracellular spaces and a few hours to be eliminated through the kidneys. The agent is routinely used in brain MRI studies to highlight areas of inflammation and in cardiac MR studies to delineate myocardial regions injured by prolonged ischemia. Gadolinium-DTPA has an appropriate safety profile and except for occasional nausea, does not cause side effects leading to discomfort or complications in patients.

Imaging of ablated lesions may be further enhanced by use of thermal imaging techniques. Thermal imaging can be accomplished by using phase differences in MR signals.

Figure 7:
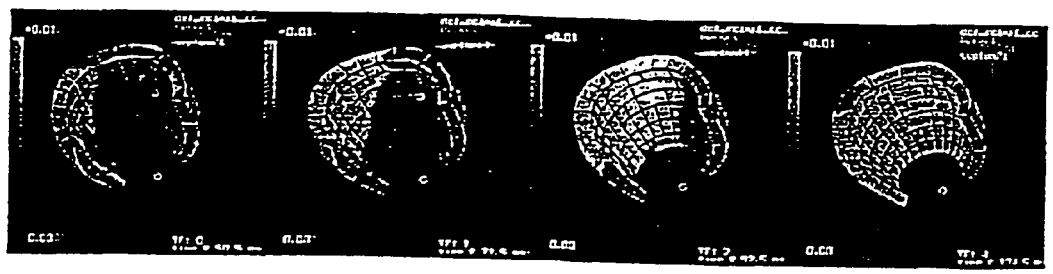
FIG. 7 shows three-dimensional reconstructions of MR images from planar sections.

Three-dimensional image reconstruction can be performed using the system and method of the invention. FIG. 7 shows three-dimensional reconstructions of MR images from planar sections. In particular, FIG. 7 shows three-dimensional reconstructions of images during activation of the left ventricle from a right ventricular pacing site. In FIG. 7, the white areas show the spread of mechanical activation as the wave of electrical activation spreads across the left ventricle from the right ventricular pacing site. Similar image processing techniques can be used for visualizing ablated areas.

The advantages of the system and method for MR-guided electrophysiology in accordance with the invention will now be discussed in further detail.

Recent advances in MRI technology enable frame rates higher than 10/sec. This exceeds the frame rate often used in current pulsed x-ray fluoroscopy systems. When the depth dimension of the MRI slice is set as large as the body depth, the resulting 2-dimensional image sequence can serve as an effective substitute for x-ray fluoroscopy.

The system can thus facilitate catheter placement for EP study with real-time imaging, without the need for ionizing radiation. Catheters used in this system must be composed entirely of non-ferromagnetic materials, so as not to perturb the electromagnetic gradient field required for distortion-free MR imaging.

MRI allows for precise localization of object elements in three-dimensional space. Catheter tip position within the heart can thus be determined accurately and precisely, and can then be displayed superimposed on anatomically accurate reconstructions of cardiac architecture. This functionality is not possible with x-ray fluoroscopy.

Electrical activation timing information obtained via an EP mapping catheter, when combined with catheter localization information, enables accurate color-coded activation maps. This capability is most useful in determining the site of origin of an atrial or ventricular tachycardia.

Activation maps can be superimposed on anatomically accurate reconstructions of cardiac structure. Spatially accurate voltage data, however, requires knowledge of the location of each electrode in contract with the myocardium. This can be achieved by using high-density basket catheter electrodes in conjunction with active tracking RF coils. Each untuned electrode is capable of receiving signal, which in turn, provides the 3-space coordinates of each electrode. Electrical data originating from each known electrode position allows generation of activation and voltage maps on true anatomic structures.

This provides significant advantages beyond the capabilities of the non-fluoroscopic electroanatomic mapping system noted above, since that system does not provide accurate anatomic information, again without additional hardware.

An imaging antenna can be incorporated into a steerable mapping/ablation catheter, enabling high-resolution imaging in the region near the catheter tip. The image obtained with this antenna has a similar radius of view as that with intracardiac ultrasound, but with far greater resolution. Furthermore, this high-resolution image is obtained without the need for placement of an additional catheter, as is required with intracardiac ultrasound.

High-resolution images derived from the internal antenna can be combined with lower-resolution wide-field images obtained with the external coil into a single image.

This composite image will display the entire cardiac cross section with enhanced resolution in the area of greatest interest When the ablation/imaging catheter is used for the delivery of ablative radio-frequency energy, the high-resolution image obtained via this catheter enables visualization of the lesion and of lesion growth. It may also be possible to visualize lesions with surface coils alone, if the tissue is thick enough.

Directional orientation, as well as location, of the catheter tip can be determined in three-dimensional space. The high-resolution image data obtained via the internal antenna can be displayed in any plane, and in particular, in the plane orthogonal to the catheter. Since the image is obtained with the same catheter that is delivering the ablative energy, the orthogonal-plane image is guaranteed to display the lesion at its maximal radius, without the need to manipulate a second (imaging) catheter into alignment with the ablation catheter. Lesion size will thus not be underestimated as often occurs with intracardiac ultrasound. In the latter case, the imaging catheter differs from the ablation catheter. It is therefore not necessarily imaging at the same level as the ablation catheter tip, and is not necessarily parallel to the ablation catheter so the image plane is oblique to the lesion equator.

MR is an imaging modality that can be tuned to characterize tissue physiology as well as structure. This enables imaging of lesions by virtue of changes in structure and cell function that occur with fulguration. Injection of gadolinium further enhances the MR image contrast between healthy and ablated myocardium. Intracardiac ultrasound, on the other hand, enables visualization of lesions only to the extent that tissue echogenicity is altered.

Because the MRI-guided EP system of the invention combines two-dimensional real-time image sequences, accurate three-dimensional catheter tip localization for activation mapping, and the ability to see myocardial tissue and lesion growth, it offers the best features of x-ray fluoroscopy, the non-fluoroscopic electroanatomic mapping system, and intracardiac ultrasound all at once without ionizing radiation, extra venipunctures, or excessively expensive catheters.

High-resolution visualization of ablative lesions by the internal MR antenna allows for documentation of whether or not RF application resulted in successful lesion development and of where lesions have and have not yet been made. This facilitates efficient catheter placement so that RF is applied only to tissue not previously ablated.

The high-resolution images obtained with the internal MR antenna enables visualization of the relatively thin atrial wall. This structure may not be well visualized by the external MR coil due to lack of adequate resolution. If the atrial wall or other anatomical structures to be visualized have thick enough walls, which does occur, adequate visualization may be obtained with surface coils alone.

The combination of the high-resolution visualization and images discussed above makes high-resolution MRI guidance ideal for visualization and verification of ablative lesion lines, particularly in atrial tissue. This is useful for ablation of the reentrant circuit in typical atrial flutter and is crucial for successful ablation of atrial fibrillation.

Investigators have shown that atrial fibrillation can be eliminated with multiple lines of ablative lesions placed in the right and left atria to emulate the surgical maze procedure. Failures of the 'percutaneous maze' procedure have resulted primarily from incomplete lesion lines. MRI guidance should allow rapid confirmation of lesion line continuity and avoidance of unnecessary repetition of RF application where tissue has already been successfully ablated.

The MRI-guided catheter ablation system offers advantages in ablation of ischemic and idiopathic ventricular tachycardias, ectopic atrial tachycardias, atrial flutter, and atrial fibrillation. Unlike AV node reentry and accessory pathway mediated tachycardia, these other arrhythmias have lower ablation success rates and longer ablation procedure durations, primarily due to difficulties in accurate activation mapping or confirmation of lesion development with conventional equipment.

Procedure durations and risk of complications should thus be reduced substantially with the MRI-guided catheter ablation system.

A system and method for using magnetic resonance imaging to increase the accuracy of electrophysiologic procedures is disclosed. The system in its preferred embodiment provides an invasive combined electrophysiology and imaging antenna catheter which includes an RF antenna for receiving magnetic resonance signals and diagnostic electrodes for receiving electrical potentials. The combined electrophysiology and imaging antenna catheter is used in combination with a magnetic resonance imaging scanner to guide and provide visualization during electrophysiologic diagnostic or therapeutic procedures. The system is particularly applicable to catheter ablation of cardiac arrhythmias. In embodiments which are useful for catheter ablation, the combined electrophysiology and imaging antenna catheter may further include an ablation tip, and such embodiment may be used as an intracardiac device to both deliver energy to selected areas of tissue and visualize the resulting ablation lesions, thereby greatly simplifying production of continuous linear lesions. The system further includes embodiments useful for guiding electrophysiologic diagnostic and therapeutic procedures other than ablation. Imaging of ablation lesions may be further enhanced by use of MR contrast agents. The antenna utilized in the combined electrophysiology and imaging catheter for receiving MR signals is preferably of the coaxial or "loopless" type. High-resolution images from the antenna may be combined with low-resolution images from surface coils of the MR scanner to produce a composite image. The system further provides a system for eliminating the pickup of RF energy in which intracardiac wires are detuned by filtering so that they become very inefficient antennas. An RF filtering system is provided for suppressing the MR imaging signal while not attenuating the RF ablative current. Steering means may be provided for steering the invasive catheter under MR guidance. Other ablative methods can be used such as laser, ultrasound, and low temperatures.

Embodiments of the system and method disclosed herein include:

A method for performing an electrophysiological procedure, comprising the steps of: placing a subject in a main magnetic field; introducing an MR-compatible electrode catheter; acquiring a magnetic resonance signal; using magnetic resonance imaging to determine the location of said MR-compatible electrode catheter; and, using said MR-compatible electrode catheter to acquire electrical signals indicative of an electrophysiological state. The electrical signals may be indicative of an electrophysiological state comprise intracardiac electrograms. The MR-compatible electrode catheter may include a tip comprising gold. The MR-compatible electrode catheter may comprise an MR-visible material, such as a metal. The method may include using a magnetic resonance contrast agent to enhance images acquired in said step of using magnetic resonance imaging to determine the location of said MR-compatible electrode catheter. The method may include acquiring a magnetic resonance signal comprises the step of using a magnetic resonance imaging antenna which is integral with said MR-compatible electrode catheter.

A method for treating cardiac arrhythmias, comprising the steps of: placing a subject in a main magnetic field; introducing an ablation catheter; and, using magnetic resonance imaging to visualize ablation lesions created using said ablation catheter. The method may include using a catheter antenna to receive magnetic resonance signals, wherein said catheter antenna comprises a loopless antenna or a loop antenna. The method may also include using a magnetic resonance contrast agent to enhance the visibility of said ablation lesions in MR images, wherein the contrast agent is gadolinium-DTPA.

A system for performing ablation therapy, comprising: ablation tip means for applying ablative energy to create ablation lesions; catheter means for inserting said diagnostic electrodes into a region to be treated; magnetic resonance antenna means, integral with said catheter means, for receiving magnetic resonance signals; and, means for analyzing said received magnetic resonance signals and for displaying an image of said region to be treated, whereby said means for inserting can be guided to said region to be treated. The system for performing ablation therapy may further comprise: a plurality of diagnostic electrodes; a loopless antenna; or a means for generating RF ablation current; that includes a means for generating an RF magnetic resonance imaging signal in a first frequency range; and a filter means for filtering said first frequency range from said RF ablation current. The antenna may receive induced magnetic resonance signals and be an invasive catheter antenna, wherein the catheter antenna comprises a loopless or loop antenna. The means for generating an RF magnetic resonance imaging signal may comprises means for generating a RF magnetic resonance signal (64 MHz for 1.5 Tesla) and wherein said filter means may comprise means for filtering said resonance signal from said ablation signal. The filter means may comprise a low-pass filter, a multi-stage filter, a filter for filtering gradient-induced noise, or a filter for filtering gradient-induced noise comprises a series of active filters.

A method for performing an electrophysiological procedure, comprising the steps of: placing a subject in a main magnetic field; introducing an invasive imaging antenna; acquiring a first magnetic resonance image from said invasive imaging antenna; acquiring a second magnetic resonance image from a surface coil; combining said first and second magnetic resonance images to produce a composite image; and, using said composite image to guide said electrophysiological procedure. The step of using said composite image to guide said electrophysiological procedure may comprise using said composite image to guide an ablation procedure, such as to construct a three-dimensional map of areas in the heart that have undergone ablation or to construct a three-dimensional rendering of the heart. The method may include storing said three-dimensional rendering into a texture map of an imaging volume.

A system for magnetic resonance imaging-guided catheter ablation, comprising: electrode means for receiving electrical signals indicative of an electrophysiological state, said electrical signals being within a first frequency range; means for generating an RF magnetic-resonance-inducing signal; magnetic resonance antenna means for receiving magnetic resonance signals from a region to be treated; filter means for filtering said first frequency range from said RF magnetic-resonance-inducing signal.

A combined electrophysiology and imaging catheter, comprising: at least one diagnostic electrode; catheter for inserting said diagnostic electrode into a region to be studied; and, an invasive magnetic resonance antenna, integral with said catheter, for receiving magnetic resonance signals. The combined electrophysiology and imaging catheter may further comprise: steering device for deflecting said catheter, whereby said catheter can be steered to said region to be studied, such as by a steering wire, wherein said steering wire is of a titanium or other non-magnetic construction and is housed in a sheath. The steering device may comprise a steering knob that is operable to move a steering wire toward or away from a distal tip of said catheter. The combined electrophysiology and imaging catheter may further comprise: an ablation tip for applying ablative energy to a region to be treated and a flexible antenna whip at a distal portion of said catheter. The whip may be coated with an insulating layer and comprise a tip which is formed into a J-shape to prevent perforation. The catheter and all components housed therein may be fabricated of materials having low-magnetic susceptibility. The tip may be at least 4 millimeters in length, suitable for use in RF ablation procedures and fabricated from platinum or gold.

While the invention has been particularly shown and described with reference to a preferred embodiment thereof, it will be understood by those skilled in the art that various changes in form and details may be made therein without departing from the spirit and scope of the invention.

We claim:

1. A method for performing an electrophysiological procedure on a mammalian patient having a heart comprising:
   placing the patient such that the heart is in a main magnetic field of an MRI scanner;
   introducing an MR-compatible catheter into the heart;
   acquiring a magnetic resonance image of the heart;
   using the magnetic resonance image to determine a location of said MR-compatible electrode catheter in the heart, and
   at substantially the same time that the image is acquired, simultaneously using said MR-compatible catheter to acquire electrical signals of the heart and attenuating radio frequency energy induced in the catheter by the MRI scanner.

2. The method according to claim 1, wherein said electrical signals are indicative of an electrophysiological state comprise intracardiac electrograms.

3. The method according to claim 1, wherein said MR-compatible catheter is an electrode catheter having a tip comprising gold.

4. The method according to claim 3, wherein said MR-visible material comprises a metal.

5. The method according to claim 1, wherein said MR-compatible catheter comprises an MR-visible material.

6. The method according to claim 1 further comprising attenuating a frequency induced in the catheter by the MRI scanner, wherein the attenuated frequency corresponds to a radio frequency emitted by the scanner.

7. The method according to claim 1 wherein the MR-compatible catheter comprises an intrabody MRI receive antenna, and wherein the step of acquiring a magnetic resonance image of the heart includes acquiring signal data of local tissue using the antenna.

8. The method according to claim 1 wherein the MR-compatible catheter comprises an intrabody MRI receive antenna, and wherein the step of introducing the MR-compatible catheter into the heart includes acquiring signal data of local tissue using the antenna.

9. The method of claim 1 wherein comprises at least one coil, and wherein the method further comprises electronically obtaining data from the coil and guiding the catheter to a target location using the obtained coil data.

10. A method for performing an electrophysiological procedure on a mammalian patient having a heart comprising:
positioning an MR-compatible catheter into the heart;
placing the patient such that the heart is in a main magnetic field of an MRI scanner;
acquiring a magnetic resonance image of the heart;
using the magnetic resonance image to determine a location of said MR-compatible catheter in the heart;
using said MR-compatible catheter to acquire an electrical signal of the heart while the heart is in the main magnetic field of the MRI scanner, and
simultaneously with the acquisition of the electrical signal of the heart attenuating radio frequency energy induced in the catheter by the MRI scanner.

11. The method according to claim 10 wherein said catheter is positioned after the patient is positioned in the MRI scanner.

12. The method according to claim 10 wherein said MR-compatible catheter includes an electrode tip comprising gold.

13. The method according to claim 10 wherein said MR-compatible catheter comprises an MR-visible material.

14. The method according to claim 10 wherein attenuating the RF energy includes attenuating a radio frequency induced in the catheter by the MRI scanner, wherein the attenuated frequency corresponds to a radio frequency emitted by the scanner.

15. The method according to claim 10, wherein the MR-compatible catheter comprises an intrabody antenna, and wherein the step of acquiring a magnetic resonance image of the heart employs signal data obtained from the antenna.

16. The method according to claim 15 wherein the intrabody antenna is on a distal end portion of the catheter.

17. A method for performing an electrophysiological procedure on a mammalian patient having a heart comprising:
placing the patient such that the heart is in a main magnetic field of an MRI scanner;
introducing an MR-compatible electrode catheter into the heart;
using said MR-compatible electrode catheter to acquire electrical signals of the heart while the heart is in the main magnetic field, and
attenuating radio frequency energy induced in the catheter by the MRI scanner during the acquisition of the electrical signals.

18. The method according to claim 17 wherein said electrical signals are indicative of an electrophysiological state and comprise intracardiac electrograms.

19. The method according to claim 17 wherein said MR-compatible electrode catheter includes a tip comprising gold.

20. The method according to claim 17 wherein said MR-compatible electrode catheter comprises an MR-visible material.

21. The method according to claim 17, wherein said MR-visible material comprises a metal.

22. The method according to claim 17 wherein the attenuation of the radio frequency energy includes attenuating a radio frequency induced in the catheter by the MRI scanner, wherein the attenuated frequency corresponds to a radio frequency emitted by the scanner.

23. A method as in claim 17 wherein at substantially the same time that the patient is in the MRI scanner,
acquiring a magnetic resonance image of the heart, and
using the magnetic resonance image to determine a location of said MR-compatible electrode catheter in the heart.

24. The method according to claim 17, wherein the MR-compatible catheter comprises an intrabody antenna, and the method includes acquiring an MR image of the heart using signal data from the antenna.

25. The method according to claim 24, wherein the intrabody antenna is on a distal end portion of the catheter.

26. A method for performing an electrophysiological procedure on a mammalian patient having a heart comprising:
introducing an MR-compatible catheter into the heart;
placing the patient with the catheter such that the heart is in a main magnetic field of an MRI scanner;
attenuating radio frequency energy induced in the MR-compatible catheter by the MRI scanner while the heart is in the main magnetic field.

27. The method according to claim 26 further comprising acquiring electrical signals with the catheter, where the signals are indicative of an electrophysiological state comprise intracardiac electrograms.

28. The method according to claim 26 wherein said MR-compatible catheter includes an electrode tip comprising gold.

29. The method according to claim 26 wherein said MR-compatible catheter comprises an MR-visible material.

30. The method according to claim 29 wherein said MR-visible material comprises a metal.

31. The method according to claim 26 wherein the attenuated frequency corresponds to a radio frequency emitted by the scanner.

32. The method according to claim 26 wherein at substantially the same time that the patient is in the MRI scanner,
acquiring a magnetic resonance image of the heart, and
using the magnetic resonance image to determine a location of said MR-compatible electrode catheter in the heart.

33. The method according to claim 26 wherein filters are applied to attenuate the frequencies.

34. The method according to claim 26, wherein the MR-compatible catheter comprises an intrabody antenna, and the method includes acquiring an MR image of the heart using signal data from the antenna.

35. The method according to claim 34, wherein the intrabody antenna is on a distal end portion of the catheter.

* * * * *